United States Patent [19]
Jhuboo et al.

[11] Patent Number: 5,954,527
[45] Date of Patent: Sep. 21, 1999

[54] MODULAR SYSTEM, PARTICULARLY FOR BIOMEDICAL APPLICATIONS, A UNIT AND A COMMUNICATION SYSTEM FOR USE THEREIN

[75] Inventors: Abel Nasser Jhuboo, Sanit Etienne de Saint Geoirs; Jean-Michel Dupouy, La Tronche, both of France

[73] Assignee: Fresenius AG, St. Wendel, Germany

[21] Appl. No.: 08/705,224

[22] Filed: Aug. 29, 1996

[30] Foreign Application Priority Data

Dec. 19, 1995 [EP] European Pat. Off. ............. 95120085

[51] Int. Cl.⁶ .................................................... H01R 13/44
[52] U.S. Cl. ...................... 439/144; 439/341; 439/928; 439/157; 361/732; 361/733; 361/735
[58] Field of Search ..................... 439/928, 341, 439/376, 372, 142, 144, 157; 361/728, 729, 730, 732, 733, 731, 735

[56] References Cited

U.S. PATENT DOCUMENTS

| | | |
|---|---|---|
| 3,691,471 | 9/1972 | Cicognani et al. . |
| 4,433,433 | 2/1984 | Ogawa et al. . |
| 4,501,460 | 2/1985 | Sisler . |
| 4,756,706 | 7/1988 | Kerns et al. . |
| 5,230,635 | 7/1993 | Takenouchi et al. ............. 439/372 |
| 5,242,408 | 9/1993 | Jhuboo et al. . |
| 5,254,096 | 10/1993 | Rondelet et al. . |
| 5,295,967 | 3/1994 | Rondelet et al. . |

FOREIGN PATENT DOCUMENTS

| | | |
|---|---|---|
| 0 646 382 A1 | 4/1995 | European Pat. Off. . |
| 3443 834 A1 | 7/1985 | Germany . |

Primary Examiner—Paula Bradley
Assistant Examiner—Katrina Davis
Attorney, Agent, or Firm—Kenyon & Kenyon

[57] ABSTRACT

A modular system (10) is disclosed for use, e.g. in infusion systems. The system includes a base unit (20) and one or more modules (30). A mechanical/electrical connecting system (21 to 24) is disclosed enabling safe connection of the various units in the system while enabling easy disconnection of any of the modules (30). A signal processing arrangement is also disclosed enabling the number of modules (30) in the system to be sensed by the base unit (20).

30 Claims, 8 Drawing Sheets

MODULAR SYSTEM, PARTICULARLY FOR BIOMEDICAL APPLICATIONS, A UNIT AND A COMMUNICATION SYSTEM FOR USE THEREIN

FIELD OF THE INVENTION

The present invention relates to modular systems and was devised by paying specific attention to the prospected use in the biomedical field, e.g. for infusion systems and the like.

Modular systems are becoming increasingly popular in several areas, including consumer electronics (e.g. hi-fi systems), laboratory equipment, computer systems and the like.

A modular system is comprised of a certain number (notionally 1 to n) modules or units, adapted for being connected, preferably both mechanically and electrically, in arrangements selected by the user depending on specific system requirements. The modules may be either identical or different fulfilling different requirements. Any of the modules in the system may be a stand-alone component, including all the elements ensuring proper operation of the module itself and/or be adapted for operating in conjunction with other modules.

BACKGROUND OF THE INVENTION

The present invention specifically tackles the problem of providing proper interaction of the various units in a modular system especially in respect of mechanical/electrical connection of these units.

As indicated, the invention was devised with close attention to the prospected use in the biomedical area, e.g. in infusion systems, where the modules may be constituted by syringe pumps (e.g. of the kind disclosed in any of U.S. Pat. Nos. 5,242,408, 5,254,096, 5,295,967 or EP-A-0 646 382), other types of infusion pumps (such as peristaltic pumps or the like) and related medical devices (e.g. monitoring systems).

While the scope of the invention is not strictly limited to that area of prospected use, certain factors such as:

safely and securely ensuring mechanical connection of the various units arranged in a stack;

enabling rapid and easy insertion/removal of any unit in and from the system, and proper electrical connection (including but not limited to power supply and exchanging monitoring signals between the various units in the system), are of paramount importance in biomedical systems in avoiding damages to the patient, especially in such areas such as intensive care, neo-natal care and any other areas where such systems are used.

According to the present invention, such a problem is solved by means of a modular system having the features set forth in the annexed claims. The invention also relates to a unit and a communication system for use in such a modular system.

BRIEF DESCRIPTION OF THE DRAWING

The invention will now be described with reference to the enclosed drawings, wherein.

DETAILED DESCRIPTION OF THE PREFERRED EMBODIMENT

Figure 1:
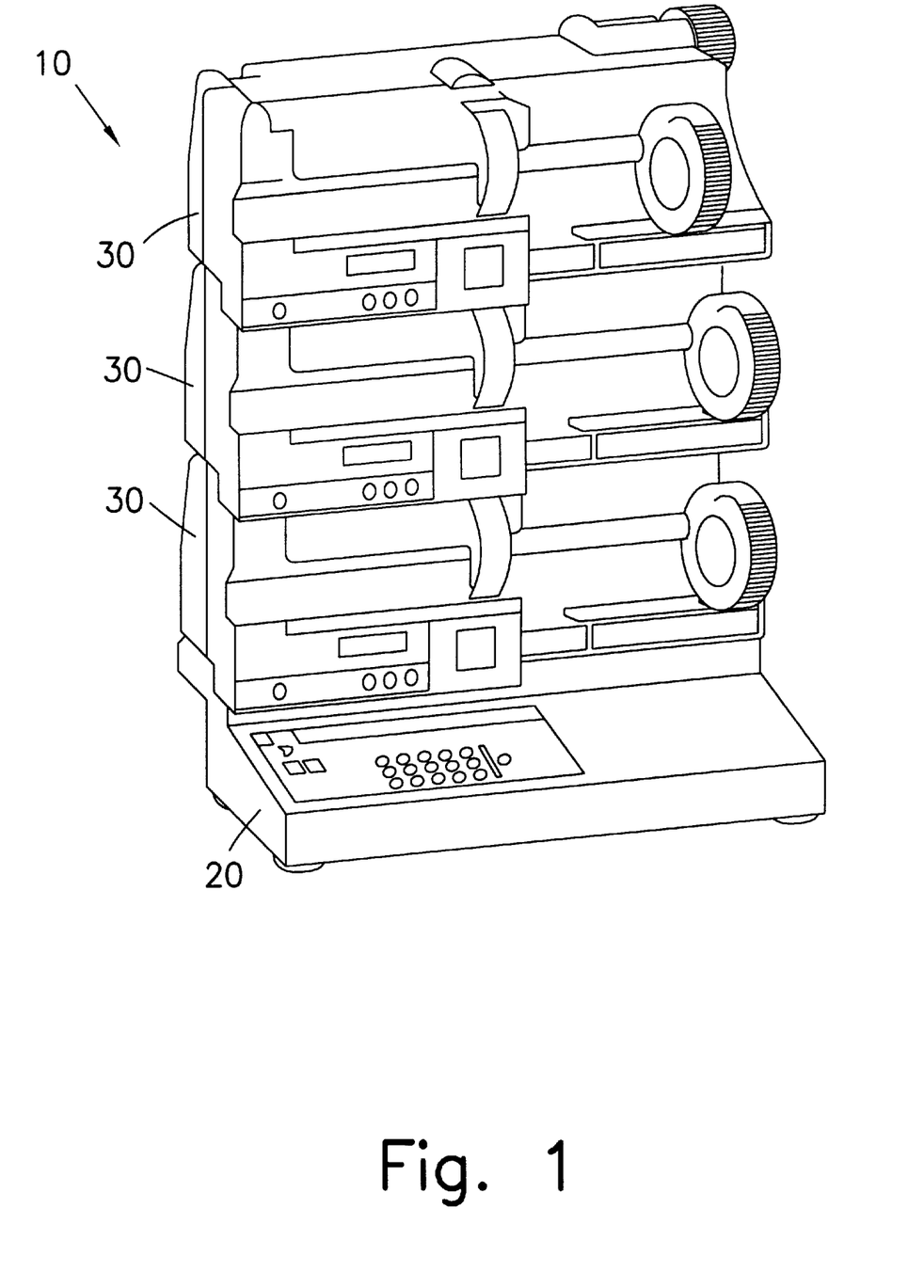
FIG. 1 schematically portrays a modular system according to the invention.

In FIG. 1 a modular system for use in biomedical applications is schematically designated 10. In the embodiment shown, system 10 is essentially comprised of a base unit 20 onto which a number of modules 30 are stacked.

In the exemplary embodiment shown, modules 30 are each comprised of a syringe pump of the kind disclosed, e.g. in the prior art documents cited in the introductory part of the description. Even though the present detailed description will generally refer to such modules, the invention is suitable for use in connection of any kind of modules, such as modules different from syringe pumps, such as, e.g. infusion pumps including peristaltic pumps and the like, monitoring units, etc. Also, modules 30 can be either identical, as is the case of the exemplary embodiment shown, or different, no limitations whatsoever existing for any combination of identical/different modules.

Any number of modules 30 (notionally 1 to n) can be assembled in the system. For reasons of practicality, a maximum number of modules admitted for proper operation of system 10 will however be foreseen, e.g. six modules (the figure indicated not constituting a limiting feature of the invention). The possibility of detecting the number of modules in the system is a preferred feature of the system itself as explained in the following.

In the exemplary embodiment shown, base unit 20 essentially plays an ancillary role by providing dc power supply to modules 30, while also displaying monitoring signals indicative of operation of modules 30. Also, base unit 20 may play the role of a server unit ensuring exchange of data to and from modules 30, for instance in connection with a remote control unit such as a personal computer (not shown).

Use of base unit 20, even though a preferred option, is not mandatory. For that reason, in the following description, base unit 20 as well as modules 30 will be generally referred to simply as "unit", without making any specific distinctions between the respective roles in the modular system.

As it will be appreciated from the following description, the connection system of the invention generally provides for the presence of two complementary parts. While each module 30, intended to be located in any position in a stack, is generally provided with both complementary parts, located at the lower side and the upper side thereof respectively, base unit 20, intended to be located at the bottom of the stack, will be generally provided with only one of those two complementary parts, e.g. the same connection part located at the upper side of each module 30.

Even though locating base unit 20 at the bottom of the stack is a presently preferred option, base unit 20 may also be arranged at the top or at an intermediate position in the stack. In these latter cases, base unit 20 will generally be provided with the connection part located at the lower side of each module 30 or with both connection parts provided on modules 30. Obviously, "upper" and "lower", as used herein, refer to the usual arrangement of units 20, 30 in a vertical stack.

Figure 2:
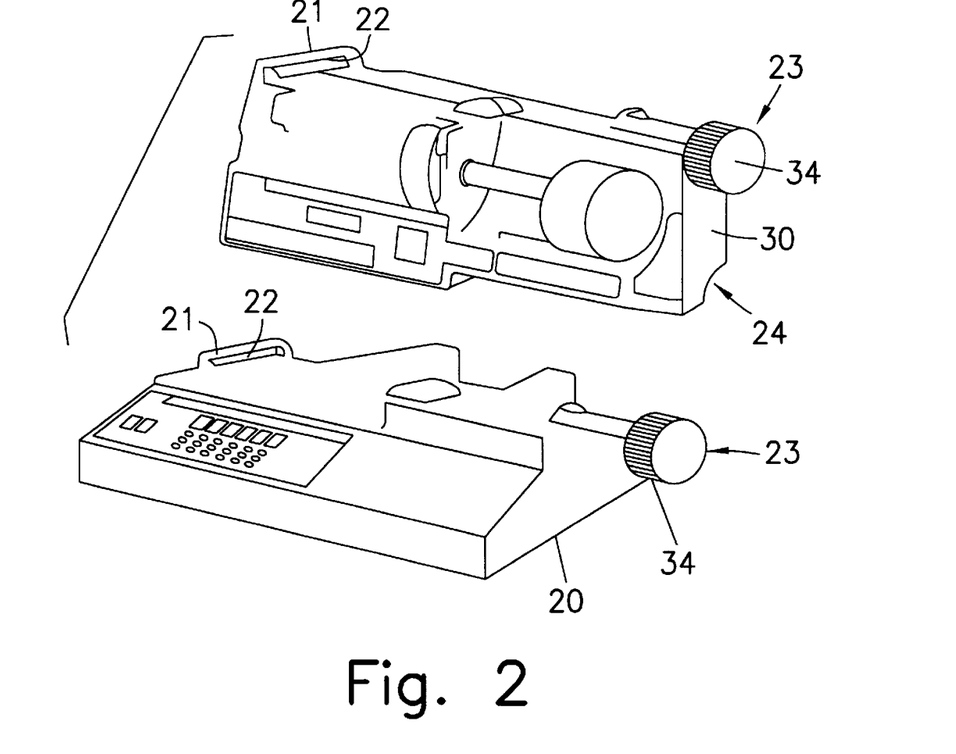
FIG. 2 shows in greater detail connection of two units in the system of the invention.

FIG. 2 shows how any of nodules 30 can be lockably mounted onto base unit 20. The same arrangement also enables mounting any of modules 30 onto an underlying module 30 (different from base unit 20). The locking arrangement described herein is thus adapted for connecting any of the "units" (as hereinbefore defined) in the system onto any underlying unit. Consequently, by suitably modifying the lower side of base unit 20 with respect to the embodiment shown in the drawing (where base unit 20 is intended to be located at the bottom of the stack formed by the units in the system), the same arrangement may also be resorted to in order to enable mounting of the base unit at the top or at an intermediate position in the stack onto an underlying module 30.

The locking arrangement shown in FIG. 2 constitutes a sort of "ski-boot" locking arrangement as it somehow resembles the arrangement used for attaching boots onto skis. Any unit in the system is provided with a housing of a preferably elongated shape thereby defining a respective front side intended to be exposed to any person attending operation of system 10. In order to enable connection, each unit 20, 30 is provided, at one end of the respective housing, with a preferably protruding shaped portion 21 that is usually integral with the moulded housing of the unit. Shaped portion 21 defines an elongated slot or cavity 22 opening towards the central region of the respective unit and extending in a generally horizontal direction in a substantially orthogonal direction with respect to the front face of the housing of the respective unit.

Even though a single protrusion 21 defining a respective single slot or cavity 22 is shown in the enclosed drawings, two or more protrusions and/or two or more slots or cavities 22 can be provided embodying the same operating principle. Use of a single protrusion 21 with a single notch or cavity 22 is a presently preferred choice as it represents a good solution in terms of reliability while avoiding unnecessary structural complexity.

Figure 4:
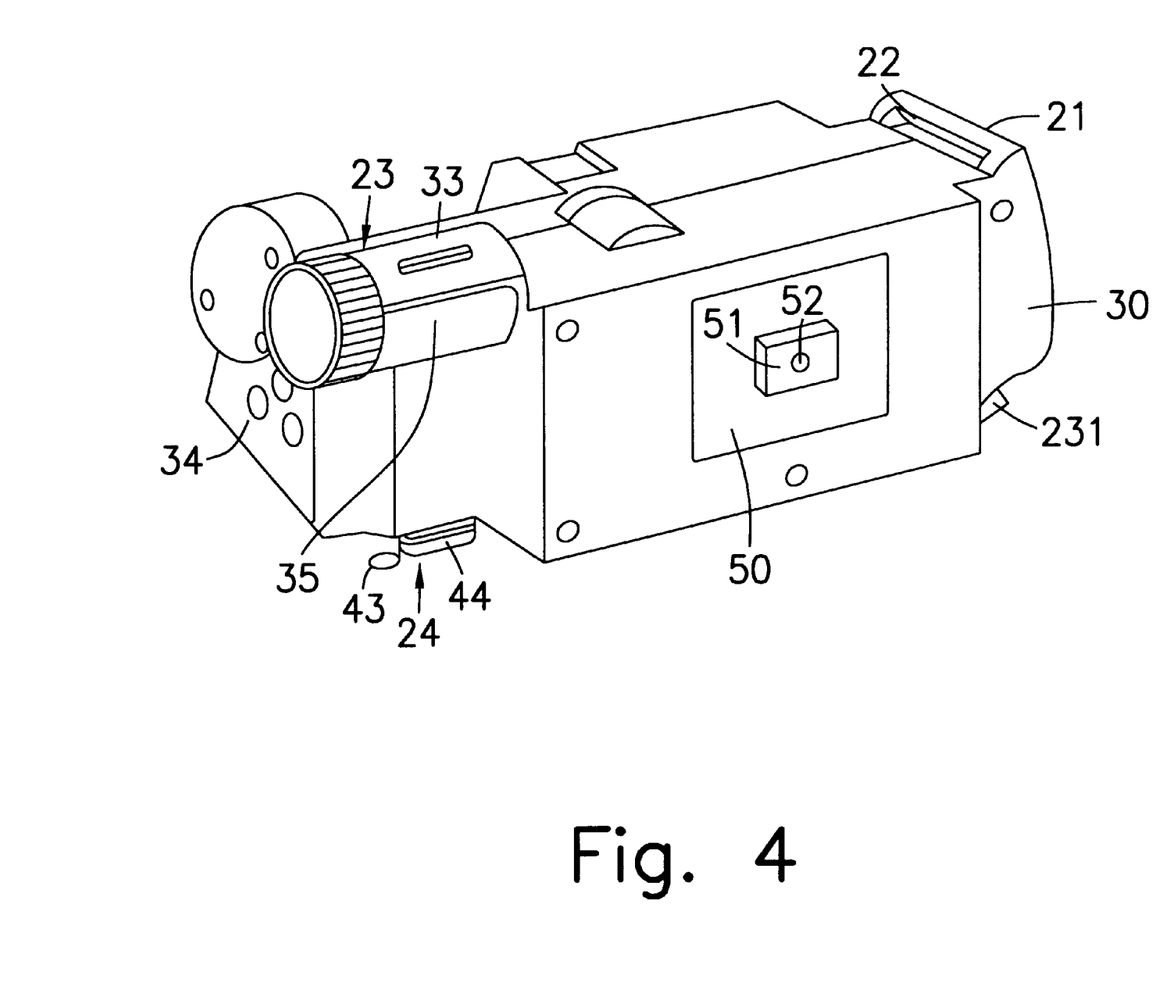
FIG. 4 is a further view of the other of the two units shown in FIG. 2.

Slot or cavity 22 provided at the upper side of the respective unit 20 or 30 is intended to receive, in a typical male/female arrangement, a respective complementary engagement formation 231 provided at a corresponding location at the lower side of each module 30 (see FIG. 4). In the embodiment shown, male formation 231 is not provided in base unit 20, as this latter unit is here intended to be located at the bottom of the stack formed by the units in the system, whereby no units are expected to be arranged thereunder.

Also, even though the embodiment shown provides for a single male formation 231 being arranged at the underside (lower side) of each module 30 to engage a respective slot 22 in the underlying unit, two or more such male formations 231 can be provided.

In mounting any of modules 30 onto an underlying unit (either base unit 20 or another module 30) male formation 231 of the upper module 30 is inserted in slot or cavity 22 of the underlying unit as schematically shown by an arrow in FIG. 2 while the end portion of the upper module opposite to male formation 231 (and slot or cavity 22) is lowered to ensure proper connection (mechanical and electrical) of two complementary parts generally designated 23 and 24.

Figure 3:
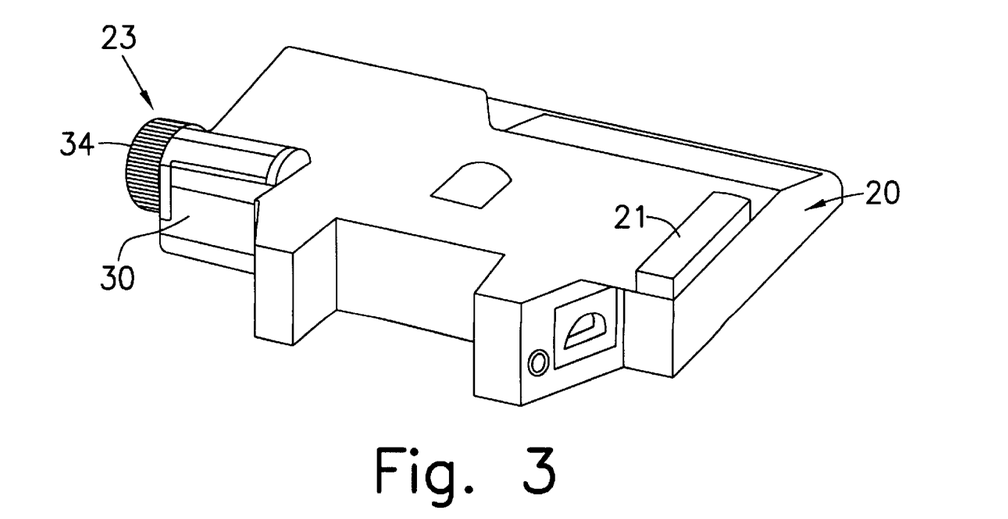
FIG. 3 is a further view of one of the two units shown in FIG. 2.

FIGS. 2 to 4 show that, in the exemplary embodiment described herein, each of modules 30 is provided with both parts 23 and 24, located at the upper and the lower sides thereof, while only part 23 is provided in base unit 20 intended to be located at the bottom of the modular system.

In the exemplary embodiment illustrated, part 23 is located at the upper side of the units 20, 30 for engagement by part 24 located at the lower side of each module 30 as the two modules involved are placed with their housing abutting one against the other in a mating relationship. The arrangement can however be reversed, thus providing a part similar to part 24 at the upper sides of base unit 20 and modules 30, these latter being provided with respective parts 23 at their lower sides. Nonetheless, the solution devised for part 23, including a rotary cover intended to be turned open when a module 30 is being mounted onto another unit is a preferred choice for mounting at the upper side of each unit 20, 30 as such a rotary cover protects the whole connection part and particularly the electrical components (plug) provided therein.

Figure 5:
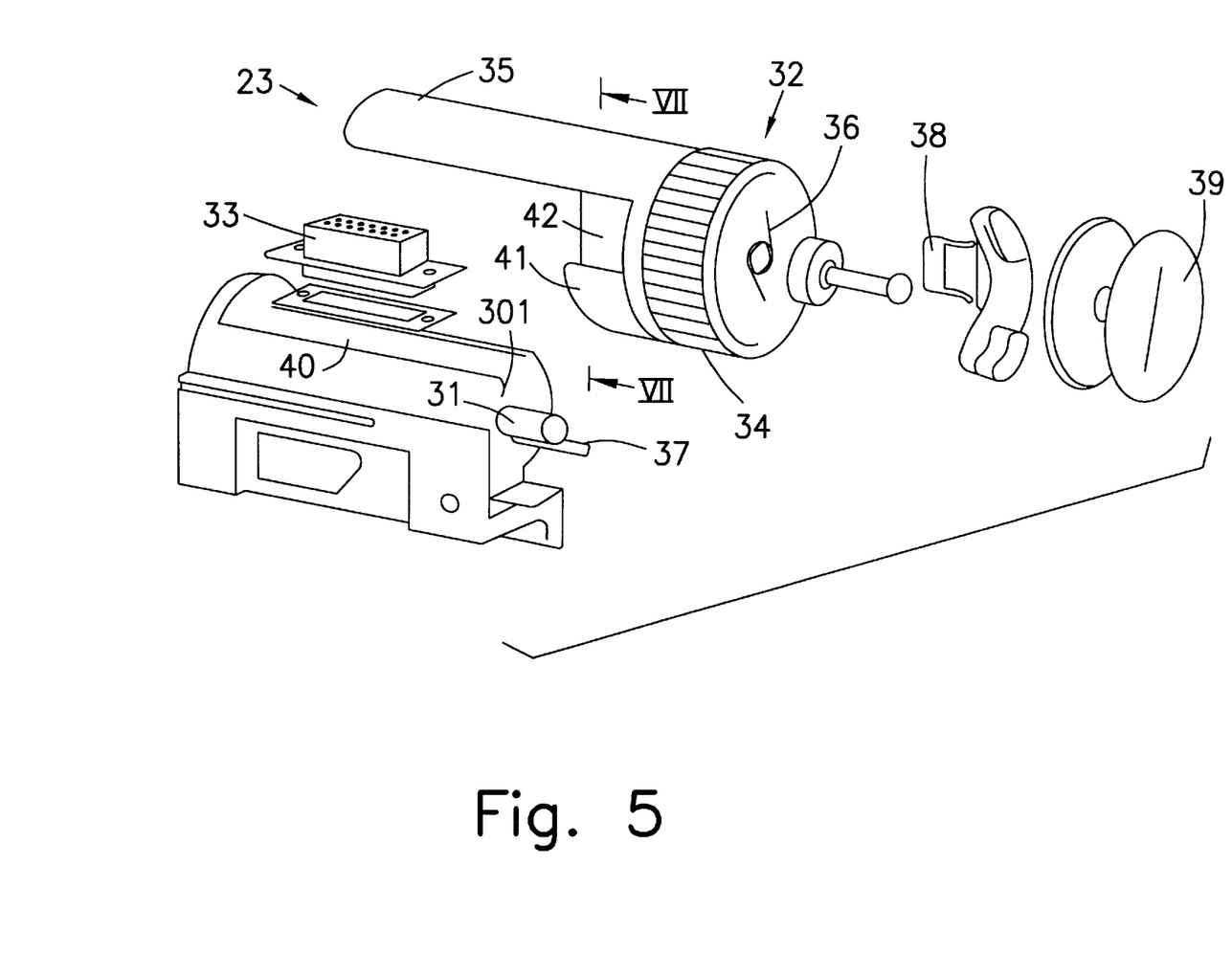
FIG. 5 is an exploded view of a part of the connection system of the invention.

Turning now to the exploded view of FIG. 5, upper connection part 23 provided on base unit 20 is shown to be essentially comprised of a supporting block made up of a cylindrical casing 301 adapted for mounting onto housing of base unit 20 with the central axis of the cylindrical casing 301 extending horizontally. Casing 301 is preferably located at the rear side of the housing of base unit 20 (the same also applying for modules 30) and is provided at its outer end with a protruding peg or shaft 31 for mounting a spring-biased rotary member generally designated 32.

Casing 301 supports, generally at the upper side thereof, a connecting plug 33 (either of the male or female type) which is generally of the multi-pin type. Plugs of the captioned type, and the related cabling/circuitry located in casing 301 are conventional in the art and do not require to be described in detail here.

Rotary member 32 is generally comprised of a cylindrical actuation knob 34 rotatably mounted on shaft 31. From knob 34 a roof-tile shaped cover portion 35 extends coaxially with shaft 31 and the outer cylindrical surface of casing 30.

Knob 34 is preferably provided with an outer fluted or ribbed surface enabling member 32 to be rotated against the elastic force of a torsion spring 36 mounted about shaft 31 and reacting against a further peg 37 extending horizontally from housing 301 in proximity of shaft 31. The element designated 38 is a magnet mounted on knob 34 and covered by a flat cover member 39. Reference 38a (shown in FIG. 6 only) designates a respective sensor mounted in casing 301 in order to detect element 38 as knob 34 is rotated towards the position shown in FIG. 8, thereby providing an electrical signal indicating connecting part 23 being in a locked position (see below). A similar arrangement is thus adopted for both parts 23 shown in FIGS. 5 and 6. Also, it will be appreciated that an equivalent arrangement, using another kind of detection arrangement (e.g. optical, mechanical, etc.), may be resorted to for detecting rotation of knob 34 to the locking position of FIG. 8.

Essentially, spring 36 acts so as to urge member 32 to rotate about shaft 31 (in a counter-clockwise direction, with respect to FIGS. 5 and 6) towards a first angular position wherein cover member 35 abuts against a ridge formation 40 provided in casing 301. In such angular position cover member 35 covers plug 33 and the portion of casing 30 immediately surrounding plug 33.

A further axially shorter element designated 41 extends from knob 34 to define, within member 32 (which is usually made of a single piece of a moulded material such as plastics material) a notch 42 generally extending along a secant plane with respect to the notional cylindrical surface defined by knob 34.

Figures 6, 7, 8:
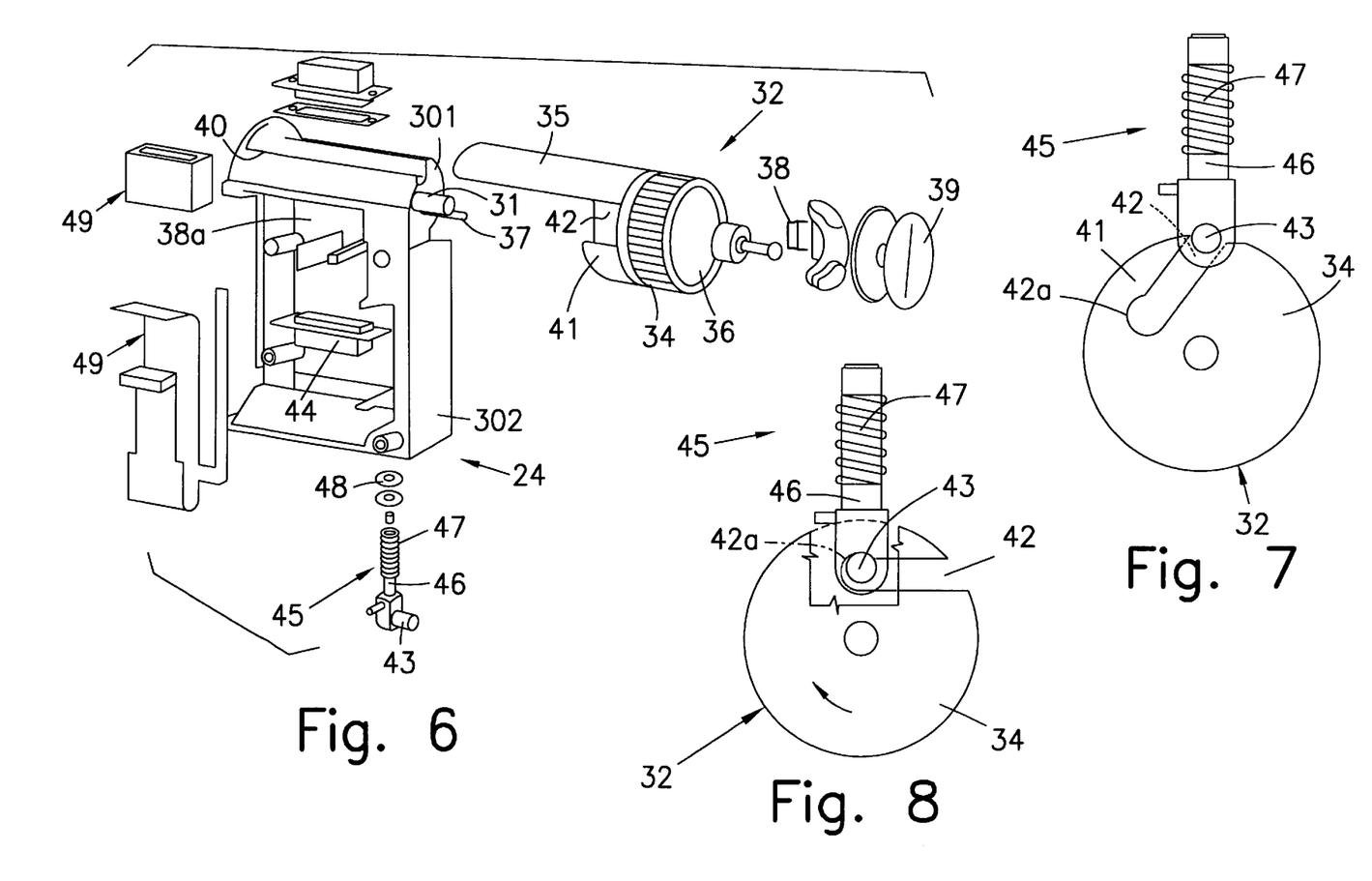
FIG. 6 is a further exploded view showing parts of the connection system of the invention.
FIGS. 7 and 8 are two schematic sectional views along line VII—VII of FIG. 5 showing operation of the connection systems of FIGS. 5 and 6.

Notch 42 is intended to act as a lock member to receive a respective male formation 43 included in connection part 24 as shown in greater detail in FIGS. 4 and 6.

In FIG. 6 the same reference numerals were used to designate the same elements or elements which are functionally identical to those already described in connection with FIG. 5.

While FIG. 5 shows only part 23, as provided at the upper side of base unit 20, FIG. 6 also shows part 24 provided at the lower side of each module 30. More specifically, as shown in FIG. 6, in modules 30 casing 301 of "upper" connection part 23 constitutes the upper portion of a larger casing adapted to be mounted at the rear side of the housing of the respective module 30 extending across the whole module thereby defining, with its lower part, generally designated 302, a further casing portion. Casing portion 302 houses a downwardly facing plug 44 that is complementary to i.e. adapted for sliding connection with plug 33 in part 23 as well a spring biased L-shaped member 45 whose distal, lower leg extends horizontally to define further male portion 43. Specifically, element 45 is provided with a vertical leg portion 46 about which a bias spring 47 is located keeping element 45 protruding outwardly of casing portion 302, while resisting any forces trying to further extract member 45 from casing portion 302. Leg portion 46 of element 45 is slidably mounted in a respective cylindrical seat (not visive in the drawing) provided in casing portion 302. Member 45 is firmly retained onto casing portion 302 by a stop nut 48 threaded onto the end of leg portion 46 extending inside casing portion 302.

Making casing 301 (in the case of part 23 as shown in FIG. 5) and casing 301–302 (as shown in FIG. 6) a self-contained member is advantageous as it enables any connection part 23, 24 possibly damaged in use to be easily replaced without having to access and to disassemble the housing of the respective unit 20, 30. For that purpose, electrical connection of casing 301 or 301-302 and the elements mounted therein (such as plugs 33, 44 and the associated cabling, if applicable) is ensured by "fast" connecting means, of known type, shown only in FIG. 6 and generally designated 49. Such fast connecting arrangements are conventional in the art and do not require to be described in detail here.

In order to lock any of modules 30 onto an underlying unit (either base unit 20 or another module 30), male formation 231 is inserted in slot 22 while the two units are caused to slide slightly along their common longitudinal direction and the opposite end of the module 30 is being lowered onto the underlying unit. That sort of "ski-boot" engagement movement brings the two connection parts 23, 24 in a mutual facing contact relationship as the two units 20 and 30 are arranged one against the other. In order to enable locking proper, rotary knob 34 in the underlying unit is rotated (in a clockwise direction, with reference to FIGS. 2, 5 and 6) thereby causing rotary member 32 to reach a second angular position wherein cover 35 uncovers plug 33 located therein and the surrounding cavity, while notch 42 reaches a respective first position (schematically shown in FIG. 7) where the open end thereof is oriented upwardly. Under these conditions, connection part 24 in the upper unit 30 can be lowered thereby engaging respective plug 44 with plug 33 in the underlying unit while further male formation 43, kept at a vertical equilibrium position by spring 47, penetrates from above into notch 42 (FIG. 7). As lowering of the upper module 30 is completed, thereby causing the respective housing to rest onto the underlying unit, knob 34 is further rotated thus causing rotary member 32 to reach a third angular position thereby orientating notch 42, having the further male formation 43 of the "upper" module slidably received therein, in a respective second angular position whereby notch 42 lies approximately in a horizontal plane (FIG. 8). At this point, male formation 43 is located at a lateral extension or cavity 42a provided at the upper side of notch 42. As male formation 43 is urged upwardly by spring 47, male formation 43 snap-engages cavity 42a, which generally extends radially with respect to rotary member 32. At this point, knob 34 is locked by male formation 43, thereby preventing rotary member 32 from rotating counter-clockwise (with reference to FIGS. 6 to 8) under the action of spring 36. Under these conditions, as male formation 43 is locked inside cavity 42a of notch 42, the "upper" module 30 is securely locked onto the underlying unit, while electrical connection between the two units thus located is ensured by connection of plugs 33 and 44.

Preferably a respective portion of the housing of each module 30 surrounding connection part 24 is shaped overall in the form of a cylindrical notch (roughly a quarter of a notional cylindrical surface) to produce a complementary shape to the cylindrical shape of the upper part of connection part 23 (cover 32 and respective part) to be inserted therein, thus ensuring a stronger form coupling between the two units locked together in a mutual facing relationship.

The two units so connected can only be separated by positively acting on knob 34 causing rotary member 32 to rotate (counter-clockwise, with reference to FIGS. 5 to 8) to overcome the releasable locking action of male formation 43 received in cavity 42a. Notch 42, acting as a lock member for formation 43, is thus brought back to the quasi-vertical position of FIG. 7, thereby releasing further male formation 43. At that point, upper module 30 can be lifted to disengage respective lower plug 44 from upper plug 33 in the underlying unit and eventually disengaging respective male formation 23 from notch 22 provided at the upper side of the underlying unit.

From the foregoing, it will be appreciated that the arrangement disclosed ensures strong and reliable connection between superposed units while providing for a simple and easy locking/unlocking procedure.

The same arrangement allows any number of modules 30 to be stacked in a column above base unit 20.

In FIG. 4 reference numeral 50 denotes a plate located on the back side of the housing of module 30 shown therein. Plate 50 may constitute a cover for a battery compartment in the module housing, and preferably carries a central butt 51 having a threaded hole therein 52. Hole 52 is adapted for receiving a screw provided in a vertical stiffening column (not shown) which may be optionally provided in order to further strengthen mechanical connection of superposed modules 30, particularly when several such modules 30 (typically four to six) are stacked. Of course other stiffening arrangement can be devised.

Figure 9:
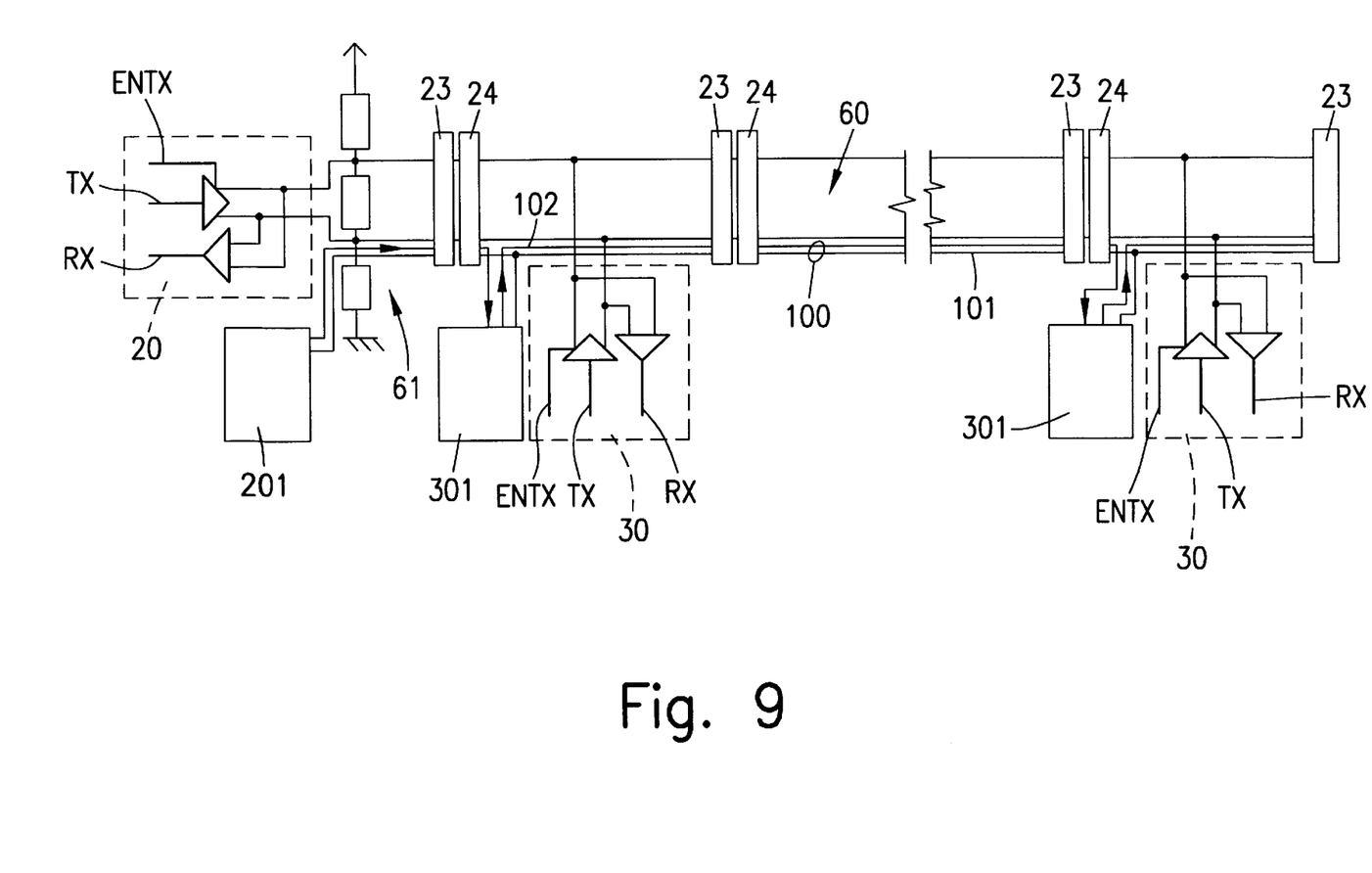
FIG. 9 shows, in the form a block diagram, the principles adopted for communication in the modular system of the invention.

The block diagram of FIG. 9 shows, in a deliberately simplified manner, electrical connection of base unit 20 with a number of modules 30: such a number is—per se—not critical to the invention.

Preferably, the arrangement of the invention provides for any of the modules 30 being operable as an independent unit, adapted for stand-alone operation. Electrical connection within the system is thus primarily meant to give any unit the possibility of transmitting/receiving information to and from any other unit in the system. This is particularly significant in the case of modules intended to operate as monitoring units, e.g. for monitoring patient oximetry and the like. Essentially, electrical connection is realized by means of connection parts 23, 24 and specifically by respective plugs 33 and 44, not shown in detail in FIG. 9.

As modules 30 can be arranged in any number onto base 20, communication of information such as digital data within the system (and possibly towards and from external equipment) takes place in a typical bus-like fashion on a common line generally designated 60 in FIG. 9.

Any well-known protocol can be used for that purpose. Essentially, all of the units in the system (the term "unit" referring again either to base unit 20 or to any of modules 30) is generally provided with respective transmission and reception ports designated TX and RX. Preferably, in a known manner, transmission port TX has associated therewith a respective enabling connection designated ENTX which enables transmission of data.

Preferably, the communication interface chosen is a low-power consumption LTC 485 buffer having the following features:
reception buffer
  high impedance whether powered or not
  resistant to input voltage reversal
  resistant to high input voltages (e.g. >5 volt)
transmission buffer
  high impedance whether powered or not
  resistant to input voltage reversal
  resistant to high input voltages (e.g. >5 volt)
  resistant to transmission on a short-circuited line.

Transmission is effected differentially on a single line as explained in the foregoing. Preferably, base unit 20 is provided with a differential adaptation resistor. Line 60 is biased by means of a pull-up/pull-down resistor arrangement generally designated 61 in order to avoid any instability when transmission buffers are deactivated.

A facility for detecting system with overload (i.e. modules in excess of a maximum number being connected to the system) is preferably provided along an additional facility for displaying in base unit 20 connection of any module 30 in the system even if the module 30 in question is not positively turned on at the moment.

As indicated, each and every module 30 is preferably comprised of a self-contained unit capable of independent, stand-alone operation i.e. even if the module is removed or disconnected from the system and/or in the absence of power supply from base unit 20.

In order to ensure proper operation of the system, especially in connection with exchange of operational data, modules 30 must be allotted proper addresses, which are to be known to base unit 20 (and possibly the other modules) Also, base unit 20 must be in a position to ascertain how many modules 30 are present in the system, and/or are activated i.a. in order to check that a maximum number of modules defined by the characteristics of the system and base unit 20 (for instance six modules) is not exceeded.

Figure 10:
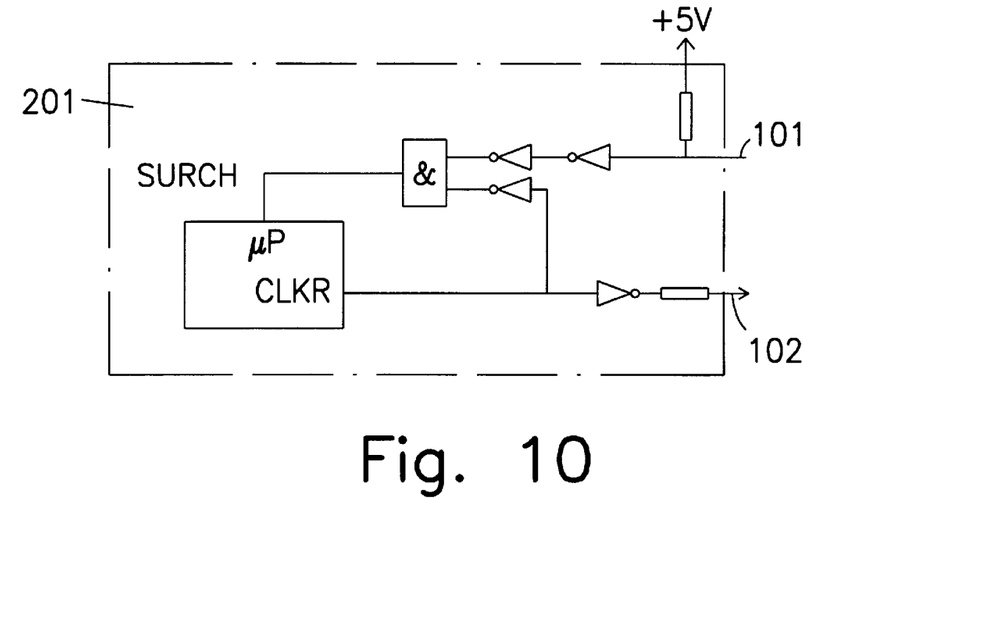
FIGS. 10 and 11 show in greater detail the structure of certain elements appearing in FIG. 9.
Figure 11:
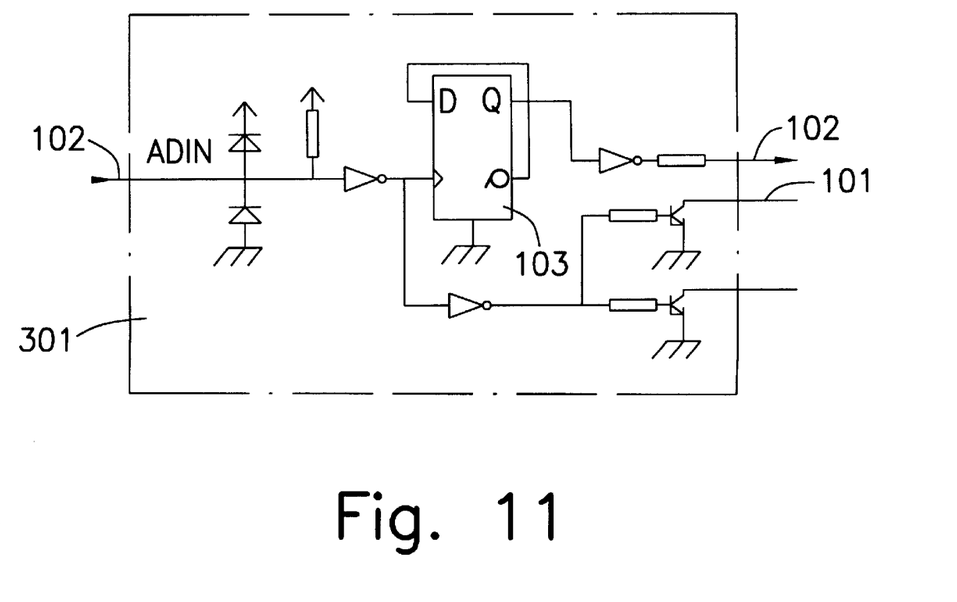

For that purpose, the various units in the system are connected (through parts 23, 24) via a further line generally designated 100, which is preferably comprised of first and second leads 101, 102 connecting respective blocks 201 (in base unit 20) and 301 (in modules 30) as shown in greater detail in FIG. 10 and 11. It will be appreciated that, while all units 20, 30 are connected to lead 101 in a bus-like arrangement, lead 102 extends from base unit 20 to and through modules 30 in a typical "daisy-chain" arrangement. Block 201 in base unit 20 generates (at output CLKR of microprocessor μP) and sends onto lead 102 towards modules 30 a signal Ti having a known frequency which is received by the module 30 located immediately above through input port designated ADIN (FIG. 11). Such module 30 sends the received signal with its frequency unaffected back towards base unit 20 over line 101 (which represents an open collector connection for all modules 30) divides (e.g. by two) the frequency of incoming signal. In the exemplary embodiment shown in FIG. 11, this is done by means of a D-type latch device 103. The resulting signal is sent over lead 102 towards any subsequent module 30 in the system. This arrangement is repeated in a cascaded manner for all the modules 30 in the system with such divided frequency. Thus, each module 30 measures the duration of the half periods of the incoming signal and consequently defines a physical address which is used for communicating over line 60.

Figure 12:
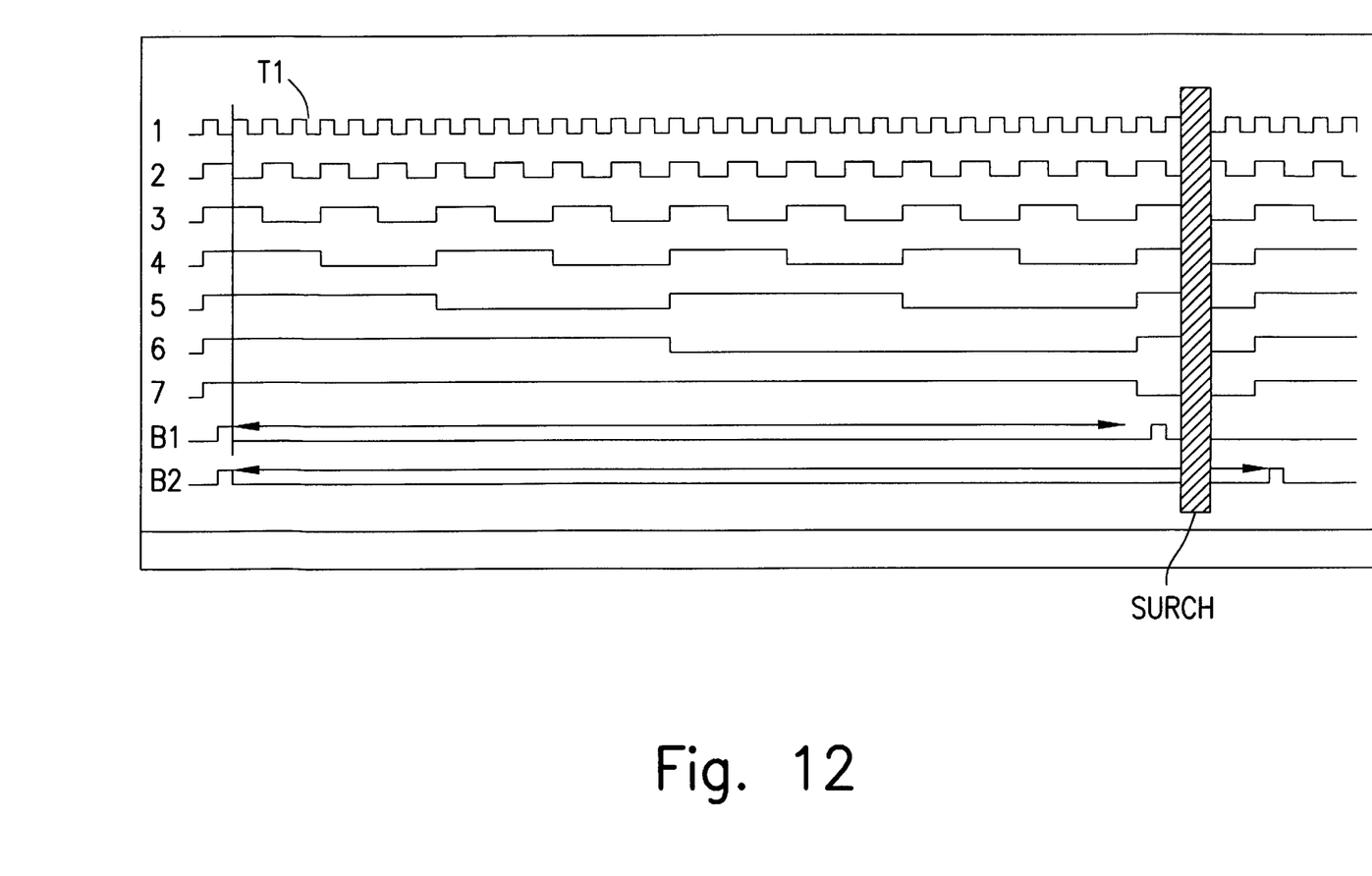
FIG. 12 is a diagram showing the time behaviour of certain signals generated within the circuit schematically shown in FIG. 9.

In the time diagram of FIG. 12 signals designated 1 to 7 schematically represent the signals returned towards base unit 20 over line 101 and thus the effect of division by two of the frequency of the basis signal generated in unit 20 by each of a respective number of modules in the system. Generally the frequency of signal T1 is chosen to be sufficiently small to be measured by real time interrupt programs operating at one millisecond. For example, T1 is chosen with a period of 10 ms which gives for the periods of the divided signals values equal to 20, 40, 80, 160, 320 ms and so on.

Due to the open collector connection of modules 30, lead 101 implements an "AND" function to give a pulse signal, such as signals designated B1 and B2 in the diagram of FIG. 12, whose period depends on the "longest" divided signal (i.e. the signal having the longest period of any signals generated by modules 30 as a result of cascaded division by two of signal T1) returned towards base unit 20 and is thus indicative of the number of modules 30.

Such a signal can be used by base unit 20 in order to ensure that the maximum number of modules 30 admitted for use in the system is not exceeded.

Specifically, in FIG. 12, signals designated B1 ad B2 correspond to the possible time behaviour of the "AND" signal present on lead 101 as sensed by base unit 20 through the input port designated SURCH in FIG. 10, where six and seven modules 30, respectively, are present (even through not necessarily activated) in the system.

A time threshold function (designated SURCH in conformity with FIG. 10) is schematically represented by a vertical bar in FIG. 12 to show how signals such as B1 or B2 may be discriminated (in a known manner) to ascertain that the maximum number of modules 30 (e.g. six in the instant exemplary embodiment) is being exceeded and to act correspondingly (i.e. sending our a warning signal).

Of course, the same function as described in the foregoing can be arranged to be performed in an equivalent manner, e.g. by different logic functions and/or using different signals, e.g. the divided signals exiting divider circuits 103 rather than the input signals to those circuits as described and shown. Also, each and every of units 20, 30 in the system can play the role described in connection with the function of base unit 20. It will also be appreciated that, in a simplified embodiment of the locking system of the invention, cover member 35 intended to cover plug 33 when any part 23 is not connected to a respective complementary part 24 may be dispensed with. In that case the first and second angular positions of member 35 may simply coincide with each other to give a single "rest" position or rotary member 32 where notch 42 is ready to receive such formation 43.

We claim:

1. A modular system (10) including at least first (20) and second (30) units having respective housings, wherein the housing of said first unit (20) carries at least a first connection part (23 resp. 24) for mechanical and electrical connection with a second, complementary connection part (24 resp. 23) carried by the housing of said second unit (30), said first and second parts (23, 24) being arranged in the respective housings in a mutual facing relationship enabling connection of said two connection parts (23, 24) as said first (20) and second (30) units are arranged one against the other, wherein the system includes a plurality of said second units (3), at least one of said second units (30) of said plurality of said second units being, provided with both said first and said second connection parts (23,24) on opposite sides thereof, whereby said units of said plurality of said second units can be arranged in a stack and wherein:

said first connection part (23) includes:
a first plug (33);
a rotary member (32) mounted in proximity of said first plug (3,3) and adapted for rotation from a first angular position towards a second angular position and further on towards a third angular position; said rotary member (32) carrying a respective lock member (42) assuming respective first and second positions as said rotary member (32) reaches said second and third angular positions, respectively; and said second connection part (24) includes:
a second lug (44) adapted for connection with said first plug (33) in said first connection part (23), and
a protruding member (43) adapted to cooperate with said lock member (42) in said first connection part (23) whereby, as said first (20) and second (30) units are arranged one against the other with said rotary member (32), in said first connection part (23) in said second angular position, said protruding member (43) in said second connection part (24) engages said lock member (42) in said first connection part (23) and as said rotary member (32) in said first connection part (23) is moved to said third angular position, the respective lock member (43) reaches said respective second position thereby locking said protruding member (43) of said second connection part (24) to said first connection part (23).

2. A modular system according to claim 1, characterised in that said rotary member (32) carries a cover member (35) for covering and uncovering said first plug (33) as the rotary member (32) is in said first and second angular positions, respectively.

3. A modular system according to claim 1, characterized in that said rotary member (32) has associated therewith a bias element (36) elastically urging said rotary member (32) toward said first angular position.

4. A modular system according to claim 1, characterized in that said rotary member (32) has associated therewith lock means (42, 42a, 43, 47) for releasably locking said rotary member (32) in said third-angular position.

5. A modular system according to claim 4, characterised in that said lock means include:

a notch (42) in said rotary member (32) for receiving said protruding member (43) extending along a generally secant plane with respect to said rotary member (32) and having a cavity (42a) extending radially to said rotary member (32); and
elastic means biasing said protruding member (43) into (47) snap-engagement with said cavity (42a).

6. A modular system according to claim 1, characterized in that said first (20) and plurality of second (30) units include generally elongated housings having first and second end portions aligned along a direction and in that said first and/or second connection parts (23, 24) are located at said first end portion of the respective housing, while the housing of said first unit (20) and at least one of said plurality of second units (30) carry at least a first further connection part (21, 22) for mechanical connection with a second, complementary further connection part (231) carried by the housing of at least one of said plurality of second units (30) due to a general respective sliding movement of said first (20) and/or second (30) unit in said direction.

7. A modular system according to claim 6, characterized in that said first further connection part includes at least one notch (22) in the respective housing and said second further connection part includes at least one male formation (231) configured to engage said notch (22).

8. A modular system according to claim 6, characterized in that said at least one of said plurality of second units (30) is provided with both said first and said second further connection parts (20, 21, 231) on opposite sides thereof.

9. A modular system according to claim 1, characterized in that each of said plurality of units (30) includes both said first and said second connection parts (23, 24), whereby the units of said plurality of second units (30) can be arranged in a stack in any respective order.

10. A modular system according to claim 1, characterized in that both of said first and second connection parts (23, 24) are provided in a common casing (301, 302), said common casing being releasably mounted in said respective housing.

11. A modular system according to claim 1, characterized in that it includes a base unit (20), said base unit (20) being provided with only one (23) of said first and second connection parts (23, 24).

12. A modular system according to claim 11, characterised in that said base unit (20) is provided only with said first connection part (23).

13. A modular system according to claim 11, characterized in that said only one of said first and second connection parts (23, 24) is provided in a respective casing (301), said respective casing being releasably mounted in said respective housing.

14. A modular system according to claim 11, characterized in that said base unit (20) is provided with only one of said first and said second further connection parts (21, 22, 231).

15. A system according to claim 14, characterised in that said base portion is provided only with said first further connection part (21, 22).

16. A unit (20, 30) for use in a modular system, said unit having a respective housing, wherein said housing carries at least one of a first (23 resp. 24) and a second (24 resp. 23) connection part each for mechanical and electrical connection with a complementary connection part carried by the housing of at least one further unit in the system, said at least one of a first and a second connection parts (23, 24) being arranged in said housings in a facing relationship enabling connection with said complementary connection part (23, 24) as said unit and said further unit are arranged one against the other, wherein:

said first connection part (23) includes:
   a first plug (33);
   a rotary member (32) mounted in proximity of said first plug (33) and adapted for rotation from a first angular position towards a second angular position and further on towards a third angular position; said rotary member (32) carrying a respective lock member (42) assuming respective first and second positions as said rotary member (32) reaches said second and third angular positions, respectively; and
said second connection part (23) includes:
   a second plug (44) adapted for connection with said first plug (33) and
   a protruding member (43) adapted to cooperate with said lock member (42) in said first connection part (23) whereby, as said unit and said further unit are arranged one against the other with said rotary member (32) in said first connection part (23) in said second angular position, said protruding member (43) in said second connection part (24) engages said lock member (42) in said first connection part (23) and as said rotary member (32) in said first connection part (23) is moved to said third angular position, the respective lock member (43) reaches said respective second position thereby locking said protruding member (43) of said second connection part (24) to said first connection part (23).

17. A unit according to claim 16, characterised in that said rotary member (32) carries a cover member (35) for covering and uncovering said first plug (33) as the rotary member (32) is in said first and second angular positions, respectively.

18. A unit according to claim 17, characterized in that said rotary member (32) has associated therewith a bias element (36) elastically urging said rotary member (32) toward said first angular position.

19. A unit according to any of claim 16, characterized in that said rotary member (32) has associated therewith lock means (42, 42a, 43, 47) for releasably locking said rotary member (32) in said third angular position.

20. A unit according to claim 19, characterised in that said lock means include:
   a notch (42) in said rotary member (32) for receiving said protruding member (43) extending along a generally secant plane with respect to said rotary member (32) and having a cavity (42a) extending radially to said rotary member (32); and
   elastic means biasing said protruding member (43) into (47) snap-engagement with said cavity (42a).

21. A unit according to claim 16, characterized in that said unit includes a generally elongated housing having first and second end portions aligned along a direction in that said first and/or second connection parts (23, 24) are located at said first end portion of said housing, while said housing carries at least a first further connecting part (21, 22) for mechanical connection with a second complementary further connection part (231) carried by the housing of said further unit (30), due to a general respective sliding movement of said unit and said further unit in said direction.

22. A unit according to claim 21, characterised in that said first further connection part includes at least one notch (22) in said housing and said second further connection part includes at least one male formation (231) adapted for engaging said at least one notch (22).

23. A unit according to claim 21, characterized in that said unit is provided with both said first and said second further connection parts (20, 21; 231) on opposite sides thereof.

24. A unit according to claim 21, characterized in that said unit is provided with only one of said first and said second further connecting parts (21, 22, 231).

25. A unit according to claim 24, characterised in that said unit is provided only with said first further connecting part (21, 22).

26. A unit according to claim 16, characterized in that said unit is provided with both said first and said second connection parts (23, 24) on opposite sides thereof, whereby any said further unit can be locked to said unit on either side thereof.

27. A unit according to claim 26, characterised in that both of said first and second connection parts (23, 24) are mounted on a common casing (301, 302), said common casing being releasably mounted on said respective housing.

28. A unit according to claim 16 characterized in that said unit (20) is provided with only one (23) of said first and second connection parts (23, 24).

29. A unit according to claim 28, characterized in that said unit (20) is provided only with said first connection part (23).

30. A unit according to claim 28, characterized in that said only one of said first and second connection parts (23, 24) is provided in a respective casing (301), said respective casing being releasably mounted in said respective housing.

* * * * *